US009718987B2

(12) United States Patent
Webster et al.

(10) Patent No.: US 9,718,987 B2
(45) Date of Patent: Aug. 1, 2017

(54) BLOCKED BIO-BASED CARBOXYLIC ACIDS AND THEIR USE IN THERMOSETTING MATERIALS

(71) Applicant: NDSU RESEARCH FOUNDATION, Fargo, ND (US)

(72) Inventors: Dean C. Webster, Fargo, ND (US); Erin Pavlacky, Lakeland Shores, MN (US); Curtiss Kovash, Jr., Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 15/160,544

(22) Filed: May 20, 2016

(65) Prior Publication Data

US 2017/0022386 A1 Jan. 26, 2017

Related U.S. Application Data

(63) Continuation of application No. 14/428,047, filed as application No. PCT/US2013/060219 on Sep. 17, 2013, now abandoned, application No. 15/160,544, which is a continuation of application No. 14/801,306, filed on Jul. 16, 2015, which is a continuation of application No. 13/577,043, filed as application No. PCT/US2011/023753 on Feb. 4, 2011, now Pat. No. 9,096,773.

(60) Provisional application No. 61/702,082, filed on Sep. 17, 2012, provisional application No. 61/302,124, filed on Feb. 6, 2010, provisional application No. 61/355,453, filed on Jun. 16, 2010, provisional application No. 61/355,487, filed on Jun. 16, 2010, provisional application No. 61/435,338, filed on Jan. 23, 2011.

(51) Int. Cl.

| C08G 63/02 | (2006.01) |
|---|---|
| C09D 163/08 | (2006.01) |
| C08F 222/02 | (2006.01) |
| C07C 69/34 | (2006.01) |
| C07C 69/40 | (2006.01) |
| C07C 69/42 | (2006.01) |
| C07C 69/44 | (2006.01) |
| C07C 69/46 | (2006.01) |
| C07C 69/48 | (2006.01) |
| C07C 69/50 | (2006.01) |
| C07C 69/704 | (2006.01) |
| C07D 307/68 | (2006.01) |
| C08F 216/12 | (2006.01) |

(52) U.S. Cl.
CPC .......... *C09D 163/08* (2013.01); *C07C 69/34* (2013.01); *C07C 69/40* (2013.01); *C07C 69/42* (2013.01); *C07C 69/44* (2013.01); *C07C 69/46* (2013.01); *C07C 69/48* (2013.01); *C07C 69/50* (2013.01); *C07C 69/704* (2013.01); *C07D 307/68* (2013.01); *C08F 222/02* (2013.01); *C08F 216/12* (2013.01)

(58) Field of Classification Search
CPC .............................. C08L 63/00; C08F 283/10
USPC ........ 523/400; 525/119, 124, 127, 167, 175, 525/176, 206, 208, 209, 212, 217
See application file for complete search history.

(56) References Cited

U.S. PATENT DOCUMENTS

| 3,209,015 A | 9/1965 | Wilbur |
|---|---|---|
| 3,223,657 A | 12/1965 | Weisfeld et al. |
| 3,236,795 A | 2/1966 | Graver |
| 3,248,404 A | 4/1966 | Werdelmann et al. |
| 3,792,041 A | 2/1974 | Yamagishi et al. |
| 3,870,664 A | 3/1975 | Faulkner |
| 4,117,029 A | 9/1978 | Kitano |
| 4,517,360 A | 5/1985 | Volpenhein |
| 4,663,072 A | 5/1987 | Cheung |
| 5,318,808 A | 6/1994 | Crivello et al. |

(Continued)

FOREIGN PATENT DOCUMENTS

| JP | H11140020 A | 5/1999 |  |
|---|---|---|---|
| JP | 2008169134 A | 7/2008 |  |
| JP | 2011190440 A | 9/2011 |  |
| WO | 2010/003728 A1 | 1/2010 |  |
| WO | 2011/097484 A1 | 8/2011 |  |
| WO | WO 2011097484 | * 8/2011 | ........... C08G 59/027 |

OTHER PUBLICATIONS

International Search Report and Written Opinion of PCT/US2013/060219 dated Jan. 24, 2014.

(Continued)

*Primary Examiner* — Terressa Boykin
(74) *Attorney, Agent, or Firm* — J.A. Lindeman & Co., PLLC

(57) ABSTRACT

This invention relates to bio-based polyfunctional carboxylic acids reacted with vinyl ether compounds to form liquid vinyl-blocked bio-based polyfunctional carboxylic acids. These liquid vinyl-blocked bio-based polyfunctional carboxylic acids can be mixed with a polyfunctional vegetable oil-based epoxy resin to form a homogeneous curable coating composition. Upon curing at elevated temperature, thermoset coatings are formed which have excellent hardness, solvent resistance, adhesion, and flexibility. The invention also relates to the use of a curable coating composition comprising at least one polyfunctional vegetable oil-based epoxy resin and at least one vinyl-blocked bio-based polyfunctional carboxylic acid, which may be coated onto a substrate and cured thermally. Methods of making the vinyl-blocked bio-based polyfunctional carboxylic acids and curable coating compositions and substrates containing the same are also disclosed.

19 Claims, 5 Drawing Sheets

(56) References Cited

U.S. PATENT DOCUMENTS

| | | | |
|---|---|---|---|
| 5,352,740 A * | 10/1994 | Ishidoya | C08L 67/00 525/119 |
| 5,646,226 A | 7/1997 | Sachinala et al. | |
| 6,077,879 A | 6/2000 | Ohtsuki et al. | |
| 6,303,777 B1 | 10/2001 | Kao et al. | |
| 9,096,773 B2 * | 8/2015 | Webster | C08G 59/027 |
| 2002/0013396 A1 | 1/2002 | Benecke et al. | |
| 2003/0229224 A1 | 12/2003 | Schaefer et al. | |
| 2006/0020062 A1 | 1/2006 | Bloom | |
| 2009/0005508 A1 | 1/2009 | Bloom | |
| 2010/0009104 A1 | 1/2010 | Greelis et al. | |
| 2011/0073253 A1 | 3/2011 | Clausi et al. | |
| 2013/0136931 A1 | 5/2013 | James et al. | |
| 2013/0203935 A1 | 8/2013 | Thiele et al. | |

OTHER PUBLICATIONS

International Preliminary Report on Patentability of PCT/US2013/060219 dated Mar. 26, 2015.
Extended European Search Report in corresponding application No. EP 13836517, dated Jun. 22, 2016.
Alpegiani et al., "1-Phenoxyethyl Esters, a New Family of Carboxy Protective Groups," Gazzetta Chimica Italiana, Societ. GBP, vol. 114, Jan. 1, 1984, pp. 391-394.
Yamamoto et al., "New thermosetting coatings using blocked carboxyl groups," Progress in Organic Coatings, vol. 40, No. 1-4, Dec. 1, 2000, pp. 267-273.
English abstract of JP 2008169134.
English abstract of JP 2011190440.
English abstract of JP 2008169134, publication date of Jul. 24, 2008.
English abstract of JP 2011190440, publication date of Sep. 29, 2011.
English abstract of JPH11140020, publication date of May 25, 1999.
English translation of JP 2011190440, publication date of Sep. 29, 2011.
International Search Report and Written Opinion for PCT International Application No. PCT/US2011/023753, dated Apr. 6, 2011.
International Search Report and Written Opinion in PCT Application No. PCT/US2014/066073 dated Feb. 23, 2015.
Busnel et al.: "Improvement of the Processing of Polyurethane Reinforced by Glass and Cellulosic Fibres," Thermosets 2011—From Monomers to Components, Proceedings of the 2nd International Conference on Thermosets, Sep. 21, 2011, 1-5, 2011. [retrieved on Jan. 12, 2015]. Retrieved from the Internet <URL: http://nparc.cisti-icist.nrc-cnrc.gc.ca/npsi/ctrl?action=rtdoc&an=18929686&lang=en>.
Hosseini et al.: "Utilization of Flax Fibers and Glass Fibers in a Bio-Based Resin," The 19th International Conference an Composite Materials 2013, 565-572, Jul. 20-Aug. 2, 2013. [retrieved on Jan. 12, 2015]. Retrieved from the Internet. <URL: http://www.researchgate.net/publication/266910697_Utilization_of_flax_fibers_and_glass_fibers_in_a_bio-based_resin>.
International Preliminary Report on Patentability in corresponding International Application No. PCT/US2014/066073, dated Jun. 2, 2016.

* cited by examiner

BLOCKED BIO-BASED CARBOXYLIC ACIDS AND THEIR USE IN THERMOSETTING MATERIALS

CROSS-REFERENCE TO RELATED APPLICATIONS

This application is a continuation of U.S. application Ser. No. 14/428,047, filed Mar. 13, 2015, which is a U.S. national phase application under 35 U.S.C. §371 of PCT/US2013/060219, filed Sep. 17, 2013, which claims priority under 35 U.S.C. §119 to U.S. Provisional Application No. 61/702,082, filed Sep. 17, 2012, which are incorporated herein by reference in their entirety. This application is also a continuation-in-part of U.S. application Ser. No. 14/801,306, filed Jul. 16, 2015, which is a continuation of U.S. application Ser. No. 13/577,043, filed Oct. 31, 2012, now U.S. Pat. No. 9,096,773, which is a U.S. national phase application under 35 U.S.C. §371 of PCT/US2011/023753, filed Feb. 4, 2011, which claims priority under 35 U.S.C. §119 to U.S. Provisional Application No. 61/302,124, filed Feb. 6, 2010; 61/355,453, filed Jun. 16, 2010; 61/355,487, filed Jun. 16, 2010; and 61/435,338, filed Jan. 23, 2011, which are all incorporated herein by reference in their entirety.

STATEMENT OF GOVERNMENT RIGHTS

This invention was made with government support under Grant Number EPS0814442 awarded by the National Science Foundation. The government has certain rights in the invention.

FIELD OF THE INVENTION

This invention relates to bio-based polyfunctional carboxylic acids reacted with vinyl ether compounds to form liquid vinyl-blocked bio-based polyfunctional carboxylic acids. These liquid vinyl-blocked bio-based polyfunctional carboxylic acids can be mixed with polyfunctional vegetable oil-based epoxy resins to form a homogeneous mixture. Upon curing the homogeneous mixtures at elevated temperature, thermoset coatings are formed which have excellent hardness, solvent resistance, adhesion, and flexibility.

The invention also relates to the use of a curable coating composition comprising polyfunctional vegetable oil-based epoxy resins and vinyl-blocked bio-based polyfunctional carboxylic acids, which may be coated onto a substrate and cured. The substrate can be any common substrate such as paper, polyester films such as polyethylene and polypropylene, metals such as aluminum and steel, glass, urethane elastomers, primed (painted) substrates, and the like.

BACKGROUND OF THE INVENTION

Due to the rising costs and depleting reserves of fossil based oil, it is desired to replace petrochemicals with chemicals based on renewable resources. Most polymers in use today are based on petrochemical derived monomers. While there has been some activity to synthesize polymer materials using bio-based raw materials, in many cases the performance properties are inferior to that of the current petrochemical based technology. Thus, there is a need for new polymers based on renewable resources that have excellent performance properties.

Vegetable oil based materials have been used a long time in paints and varnishes and in alkyd resins. Vegetable oils are derived from the seeds of various plants and are chemically triglycerides of fatty acids. That is, vegetable oils consist of three moles of fatty acids esterified with one mole of glycerol. As shown below in Formula I, fatty acids are linear carboxylic acids having 4 to 28 carbons and may be saturated or ethylenically unsaturated.

Formula I

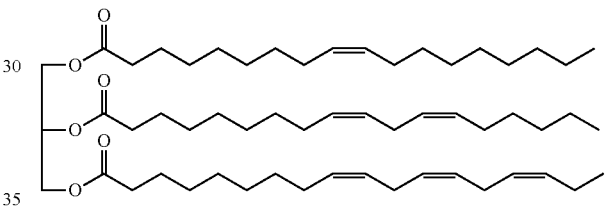

Different plants produce oils having differing compositions in the fatty acid portion of the oil. Naturally-occurring vegetable oils are by definition mixtures of compounds, as are the fatty acids comprising them. They are usually either defined by their source (soybean, linseed, etc.) or by their fatty acid composition. A primary variable that differentiates one vegetable oil from another is the number of double bonds in the fatty acid; however, additional functional groups can be present such as hydroxyl groups in castor oil and epoxide groups in vernonia oil. Table 1 below identifies the typical fatty acid composition for some commonly occurring vegetable oils.

TABLE 1

| | Fatty Acid | Unsaturation | Coconut | Corn | Soybean | Safflower | Sunflower | Linseed | Castor | Tall Oil FA | Tung |
|---|---|---|---|---|---|---|---|---|---|---|---|
| $C_{12}$ | Lauric | 0 | 44 | | | | | | | | |
| $C_{14}$ | Myristic | 0 | 18 | | | | | | | | |
| $C_{16}$ | Palmitic | 0 | 11 | 13 | 11 | 8 | 11 | 6 | 2 | 5 | 4 |
| $C_{18}$ | Stearic | 0 | 6 | 4 | 4 | 3 | 6 | 4 | 1 | 3 | 1 |
| | Oleic | 1 | 7 | 29 | 25 | 13 | 29 | 22 | 7 | 46 | 8 |
| | Ricinoleic | 1 | | | | | | | 87 | | |
| | Linoleic | 2 | 2 | 54 | 51 | 75 | 52 | 16 | 3 | 41 | 4 |
| | Linolenic | 3 | | | 9 | 1 | 2 | 52 | | 3 | 3 |
| | Eleaosteric | 3 | | | | | | | | | 80 |
| Iodine Value | | | 7.5-10.5 | 103-128 | 120-141 | 140-150 | 125-136 | 155-205 | 81-91 | 165-170 | 160-175 |

Sucrose, β-D-fructofuranosyl-α-D-glucopyranoside, is a disaccharide having eight hydroxyl groups. The combination of sucrose and vegetable oil fatty acids to yield sucrose esters of fatty acids (SEFA) as coating vehicles was first explored in the 1960s. Bobalek et al., *Official Digest* 453 (1961); Walsh et al., *Div. Org. Coatings Plastic Chem.* 21:125 (1961). However, in these early studies, the maximum degree of substitution (DS) was limited to about 7 of the available 8 hydroxyl groups. The resins do not appear to have been commercialized at that time. In the early 2000s, Proctor & Gamble (P&G) Chemicals developed an efficient process for industrially manufacturing SEFAs commercially under the brand name SEFOSE with a high DS of at least 7.7 (representing a mixture of sucrose hexa, hepta, and octaesters, with a minimum of 70% by weight octaester) (U.S. Pat. Nos. 6,995,232; 6,620,952; and 6,887,947), and introduced them with a focus on marketing to the lubricant and paint industries. Due to their low viscosities (300-400 mPa·s), SEFOSE sucrose esters can be used as binders and reactive diluents for air-drying high solids coatings. Formula II displays the possible molecular structure of a sucrose ester with full substitution. Procter and Gamble has reported a process to prepare highly substituted vegetable oil esters of sucrose using transesterification of sucrose with the methyl esters of sucrose (U.S. Pat. No. 6,995,232).

Formula II

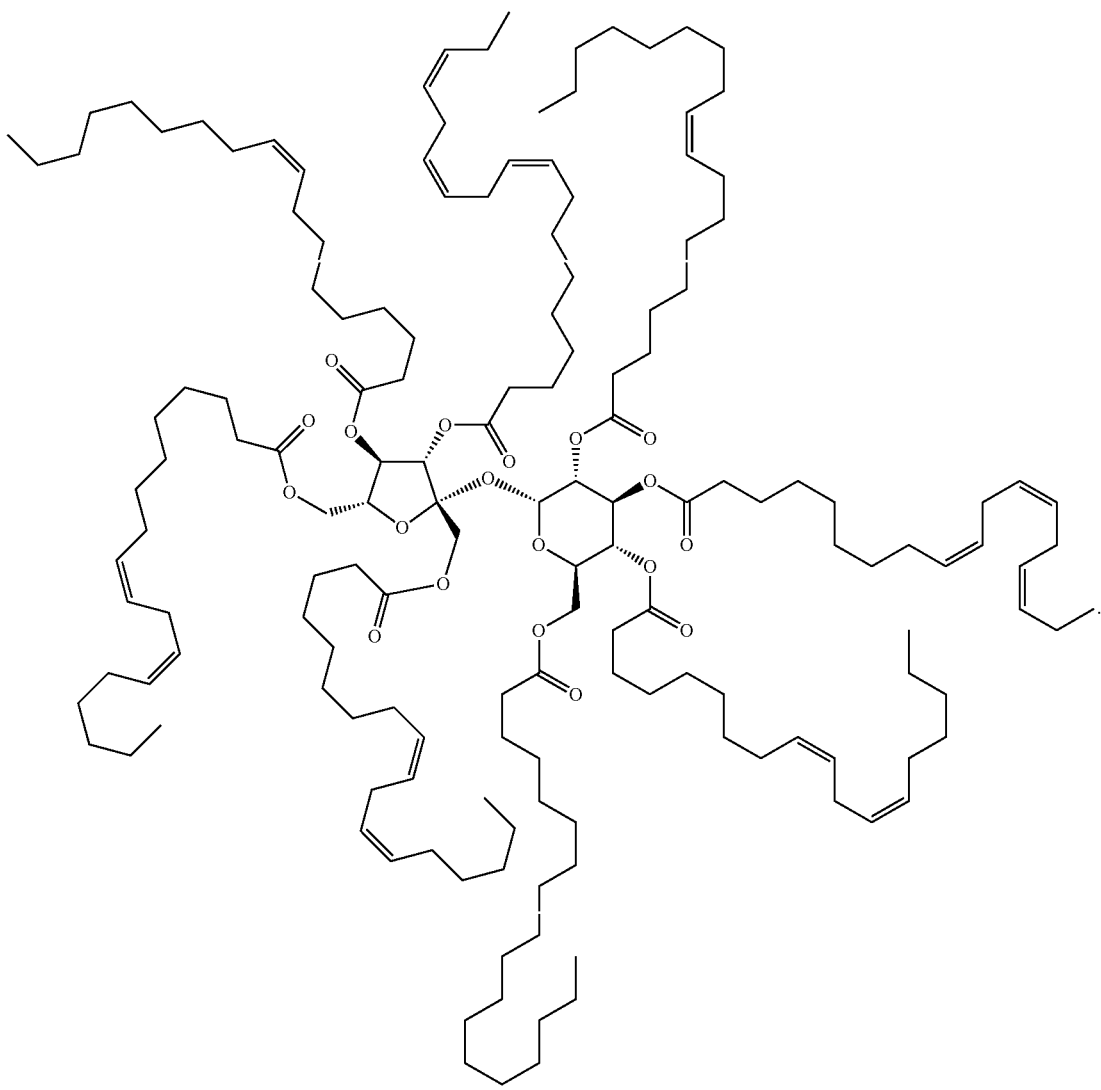

Molecular structure of sucrose ester of fatty acids

An epoxide group is a three-membered, cyclic ether containing two carbon atoms and one oxygen atom. An epoxide can also be called an oxirane. As in known in the art, an epoxy group has the structure shown in formula III in which R and R' are organic moieties representing the remainder of the compound.

Formula III

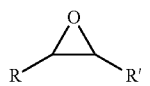

Epoxy resins are materials consisting of one or more epoxide groups. Due to the strained nature of the oxirane ring, epoxide groups are highly reactive and can be reacted with nucleophiles such as amines, alcohols, carboxylic acids. Thus, epoxy resins having two or more epoxy groups can be reacted with compounds having multiple nucleophilic groups to form highly crosslinked thermoset polymers. Oxiranes can also be homopolymerized. Epoxy resins having two or more epoxy groups can be homopolymerized to form highly crosslinked networks. Crosslinked epoxy resins are used in a large number of applications including coatings, adhesives, and composites, among others. The most commonly used epoxy resins are those made from reacting bisphenol-A with epichlorohydrin to yield difunctional epoxy resins.

Epoxidation of the double bonds in unsaturated vegetable oils results in compounds which incorporate the more reactive epoxy group. Epoxide groups, or oxirane groups, as discussed, can be synthesized by the oxidation of vinyl groups. Findley et al., *J Am. Chem. Soc.* 67:412-414 (1945), reported a method to convert the ethylenically unsaturated groups of triglyceride vegetable oils to epoxy groups, as shown in Scheme 1 below. A number of other processes and catalysts have been developed to also achieve epoxidized oils in good yields.

Scheme 1

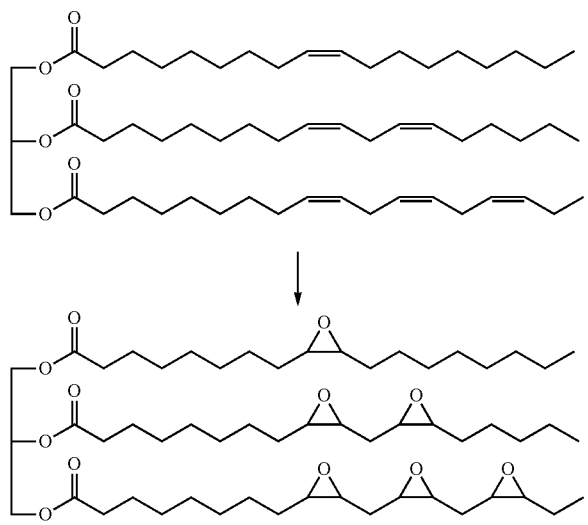

Generally, while there are four techniques that can be employed to produce epoxides from olefinic molecules (Mungroo et al., *J. Am. Oil Chem. Soc.* 85:887 (2008)), the in situ performic/peracetic acid (HCOOH or CH$_3$COOH) process appears to be the most widely applied method to epoxidize fatty compounds. Scheme 2 displays the reaction mechanism, which consists of a first step of peroxyacid formation and a second step of double bond epoxidation. Recently, the kinetics of epoxidation of vegetable oils and the extent of side reactions was studied using an acidic ion exchange resin as catalyst and revealed that the reactions were first order with respect to the amount of double bonds and that side reactions were highly suppressed; the conversion of double bonds to epoxides was also high. Petrović et al., *Eur. J. Lipid Sci. Technol.* 104:293 (2002); and Goud et al., *Chem. Eng. Sci.* 62:4065 (2007). The catalyst, Amberlite IR 120, is an acidic ion exchange resin, a copolymer based on styrene (98 wt %) crosslinked by divinylbenzene (2 wt %). Its acidity is generated by sulfonic acid groups attached to the polymer skeleton.

Scheme 2. Reactions mechanism for in situ epoxidation with peroxyacid

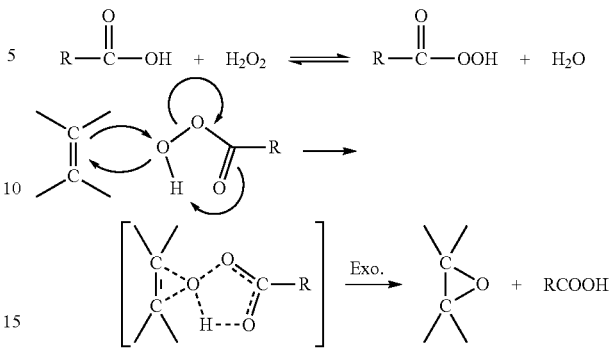

Epoxides generated from the epoxidation of double bonds of ethylenically unsaturated fatty acids are known as internal epoxides—both carbons of the heterocyclic ring are substituted with another carbon. The most commonly used epoxy resins are the bisphenol-A diglycidyl ether resins. The epoxy groups on these resins are of the type known as external epoxides—three of the four substituent groups on the heterocyclic ring are hydrogen atoms. Since internal epoxides are much less reactive than external epoxides in most epoxy curing reactions, the roles traditionally assigned to epoxidized oils are as stabilizers and plasticizers for halogen-containing polymers (i.e., poly(vinyl chloride)) (Karmalm et al., *Polym. Degrad. Stab.* 94:2275 (2009); Fenollar et al., *Eur. Polym. J.* 45:2674 (2009); and Bueno-Ferrer et al., *Polym. Degrad. Stab.* 95:2207 (2010)), and reactive toughening agents for rigid thermosetting plastics (e.g., phenolic resins). See Miyagawa et al., *Polym. Eng. Sci.* 45:487 (2005). It has also been shown that epoxidized vegetable oils can be cured using cationic photopolymerization of epoxides to form coatings. See Crivello et al., *Chem. Mater.* 4:692 (1992); Thames et al., *Surf. Coat. Technol.* 115:208 (1999); Ortiz et al., *Polymer* 46:1535 (2005).

As noted, epoxidized vegetable oils have found use as plasticizers for polyvinyl chloride (PVC). When crosslinked directly using the epoxy groups, the resulting products are relatively soft due to the aliphatic nature of the vegetable oil backbone. Epoxidized vegetable oils have been further functionalized using acrylation, methacrylation, and hydroxylation.

Epoxy resins based on polyfunctional vegetable oil esters of sucrose can be crosslinked into high performance thermosets using cyclic anhydrides. See WO 2011/097484, the disclosure of which is incorporated herein by reference.

While the epoxy resin is 100% bio-based, the system uses petrochemical derived cyclic anhydride crosslinkers, which reduces the overall bio-based content of the thermosets. It is therefore of interest to use crosslinkers which are also bio-based to form thermosets that are 100% bio-based.

There are a large number of polyfunctional acids available, which are either currently available from bio-derived processes or for which bio-based processes are being derived. Some of these acids are shown in Table 2 below. These polyfunctional acids may be used as crosslinkers for vegetable oil-based epoxy resins, such as, for example, the epoxidized vegetable oil sucrose esters, since the acid groups are reactive with the epoxy groups and the functionality is two or greater.

TABLE 2
Structures of exemplary bio-based acids
| Acid Name CAS Number | Structure |
|---|---|
| Oxalic 114-62-7 | 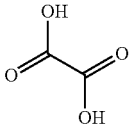 |
| Succinic 110-15-6 | 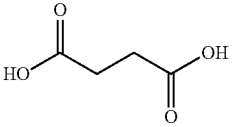 |
| Pimelic 111-16-0 | 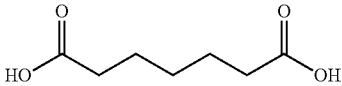 [SMILES: O=C(O)CCCCCC(=O)O] |
| Suberic 505-48-6 | 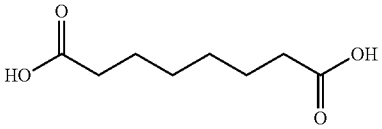 [SMILES: O=C(O)CCCCCCC(=O)O] |
| Azelaic 123-99-9 | 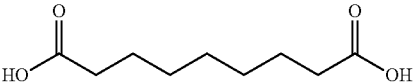 [SMILES: O=C(O)CCCCCCCC(=O)O] |
| Sebacic 111-20-6 | 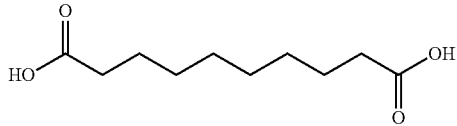 [SMILES: O=C(O)CCCCCCCCC(=O)O] |
| Brassylic 505-52-2 | 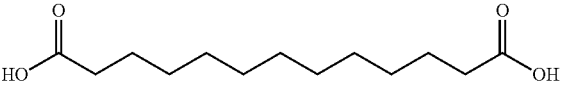 [SMILES: O=C(O)CCCCCCCCCCCC(=O)O] |
| Citric 77-92-9 | 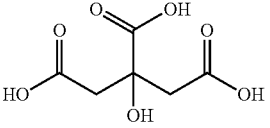 |
| Furan Dicarboxylic acid 3238-40-2 | 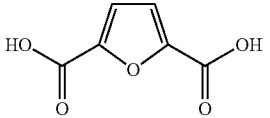 [SMILES: O=C(O)c1ccc(C(=O)O)o1] |
| Tartaric Acid 526-83-0 | 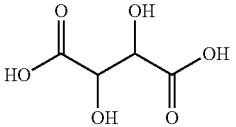 |

However, these acids are crystalline solids with high melting points, and it can be challenging to mix them with the epoxy resin and form a homogeneous mixture. Attempts at forming crosslinked materials by dispersing the diacids in the epoxy have resulted in materials with poor properties.

The reversible reaction of carboxylic acids with vinyl ether compounds leads to liquid, low viscosity materials, i.e., the carboxylic acids can be "blocked" via reactions with vinyl ether compounds. In the presence of the proper catalyst, the vinyl group can "deblock" from the carboxylic acid group and allow the acid to react with an epoxy group. See Nakane et al., *Prog. Org. Coat.* 31:113-120 (1997); Yamamoto et al., *Prog. Org. Coat.* 40:267-273 (2000), the disclosures of which are incorporated herein by reference. The blocking vinyl ether group can also be removed thermally.

SUMMARY OF THE INVENTION

In one embodiment, the invention relates to liquid vinyl-blocked bio-based polyfunctional carboxylic acids formed by the reaction of at least one bio-based polyfunctional carboxylic acid with at least one vinyl ether compound.

In another embodiment, the invention relates to a homogeneous mixture of the liquid vinyl-blocked bio-based polyfunctional carboxylic acids of the invention mixed with at least one polyfunctional vegetable oil-based epoxy resin, such as, for example, epoxidized vegetable oil sucrose ester resin. Upon curing the homogeneous mixture at elevated temperature, thermoset coatings are formed which have excellent hardness, solvent resistance, adhesion, and flexibility.

In another embodiment, the invention relates to a curable coating composition comprising at least one vinyl-blocked bio-based polyfunctional carboxylic acid and at least one polyfunctional vegetable oil-based epoxy resin. In another embodiment, the curable coating composition of the invention may be coated onto a substrate and cured using techniques known in the art. The substrate can be any common substrate such as paper, polyester films such as polyethylene and polypropylene, metals such as aluminum and steel, glass, urethane elastomers, primed (painted) substrates, and the like. The curable coating composition of the invention may be cured thermally.

In another embodiment, the invention relates to a method of making a curable coating composition of the invention comprising the step of mixing at least one vinyl-blocked bio-based polyfunctional carboxylic acid with at least one polyfunctional vegetable oil-based epoxy resin.

In another embodiment, the invention relates to thermoset coatings formed from the curable coating compositions of the invention.

In another embodiment, the invention relates to an article of manufacture comprising a thermoset coating of the invention and a method of making such article.

Other features, objects, and advantages of the invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art.

DESCRIPTION OF THE INVENTION

Terminology and Definitions

Figure 1:
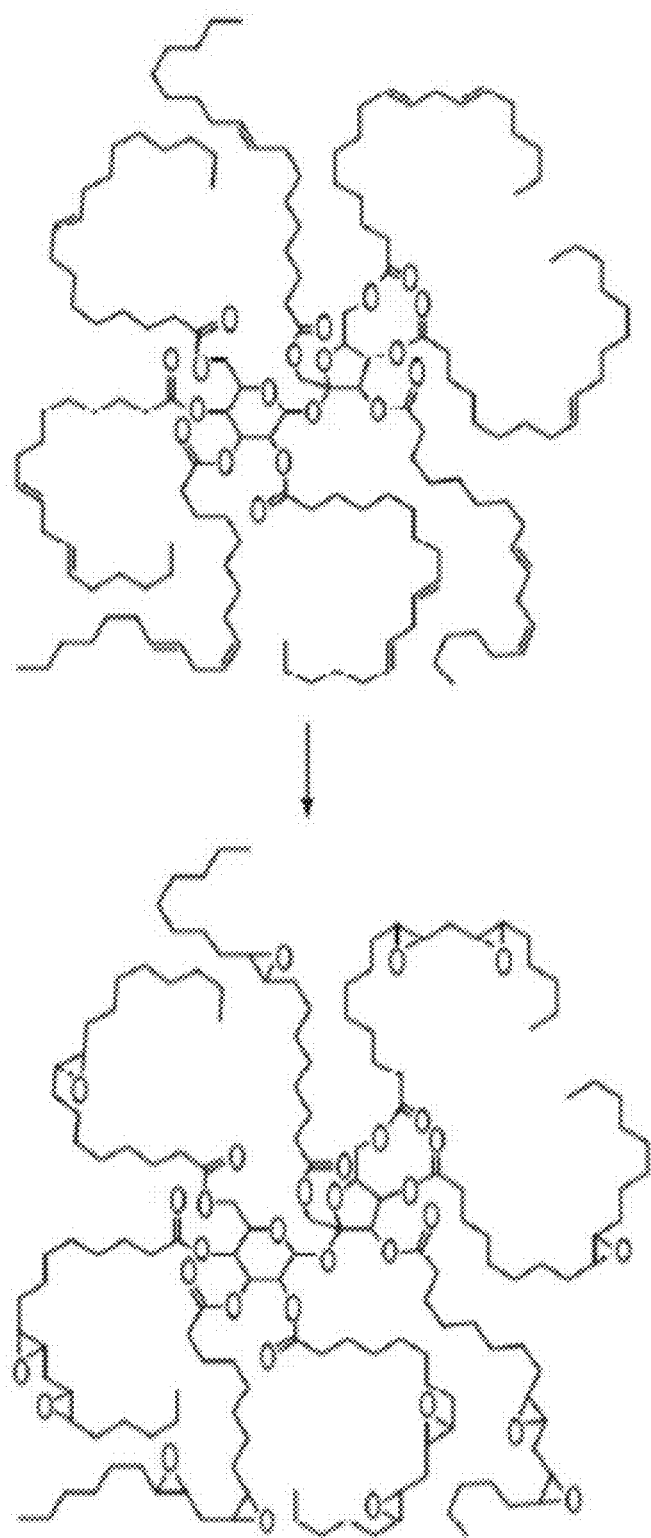
FIG. 1 depicts an exemplary epoxidation of a sucrose fatty acid ester.

Unless otherwise indicated, the invention is not limited to specific reactants, substituents, catalysts, catalyst compositions, resin compositions, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "a vinyl ether compound" includes a single vinyl ether compound as well as a combination or mixture of two or more vinyl ether compounds, reference to "a carboxylic acid" encompasses a single carboxylic acid as well as two or more carboxylic acids, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and the claims that follow, "optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Vinyl-Blocked Bio-Based Polyfunctional Carboxylic Acids

The invention relates to vinyl-blocked bio-based polyfunctional carboxylic acids comprising the reaction product of at least one bio-based polyfunctional carboxylic acid and at least one vinyl ether compound. The vinyl-blocked bio-based polyfunctional carboxylic acids are liquid at room temperature.

As used herein, a "bio-based polyfunctional carboxylic acid" means a bio-based acid comprising at least two carboxylic acid groups. For example, the bio-based polyfunctional carboxylic acid may be selected from dicarboxylic acids, tricarboxylic acids, or mixtures thereof. The dicarboxylic acids and tricarboxylic acids may be saturated or ethylenically unsaturated, optionally substituted by one or more substituents, and aromatic or non-aromatic. Unsaturation and/or substitution may occur in one or more positions anywhere on the alkyl chains of the dicarboxylic acids and tricarboxylic acids.

For example, the bio-based polyfunctional carboxylic acid may be a saturated dicarboxylic acid having the following general structure: HOOC—$(CH_2)_n$—COOH. In one embodiment, "n" may be an integer ranging from 0 to 22, preferably 2 to 16, more preferably 6 to 10. For example, the saturated dicarboxylic acid includes, but is not limited to, oxalic acid (n=0), malonic acid (n=1), succinic acid (n=2), glutaric acid (n=3), adipic acid (n=4), pimelic acid (n=5), suberic acid (n=6), azelaic acid (n=7), sebacic acid (n=8), undecanedioic acid (n=9), dodecanedioic acid (n=10), tridecanedioic acid (n=11), tetradecanedioic acid (n=12), pentadecanedioic acid (n=13), hexadecanedioic acid (n=14), heptadecanedioic acid (n=15), octadecanedioic acid (n=16), nonadecanedioic acid (n=17), icosanedioic acid (n=18), henicosanedioic acid (n=19), docosanedioic acid (n=20), tricosanedioic acid (n=21), and tetracosanedioic acid (n=22).

In another embodiment, the saturated dicarboxylic acid may be substituted by, for example, hydroxyl groups, as in tartaric acid, for example.

In another embodiment, the bio-based polyfunctional carboxylic acid may be an ethylenically unsaturated dicarboxylic acid selected from, for example, maleic acid, fumaric acid, glutanoic acid, traumatic acid, and muconic acid.

In one embodiment, the bio-based polyfunctional carboxylic acid may be selected from saturated and ethylenically unsaturated tricarboxylic acids, including, not limited to, citric acid, isocitric acid, homoisocitric acid, aconitic acid, propane-1,2,3-tricarboxylic acid, 3-carboxy-cis,cis-muconic acid, and homoaconitic acid.

In a further embodiment, the bio-based polyfunctional carboxylic acid may be selected from aromatic and non-aromatic dicarboxylic acids and tricarboxylic acids, including, but not limited to, (ortho-) phthalic acid, isophthalic acid, terephthalic acid, hemimellitic acid, trimellitic acid, trimesic acid, and 2,5-furandicarboxylic acid (FDCA).

The vinyl ether compounds may be linear, branched, or cyclic, and optionally substituted. For example, the vinyl ether compounds may have the following general structure:

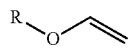

wherein R may be a liner, branched, or cyclic $C_1$-$C_{18}$-alkyl group. For example, linear vinyl ether compounds include, but are not limited to, methyl vinyl ether, ethyl vinyl ether, propyl vinyl ether, butyl vinyl ether, pentyl vinyl ether, hexyl vinyl ether, heptyl vinyl ether, octyl vinyl ether, nonyl vinyl ether, decyl vinyl ether, undecyl vinyl ether, dodecyl vinyl ether, tridecyl vinyl ether, tetradecyl vinyl ether, pentadecyl vinyl ether, hexadecyl vinyl ether, heptyl vinyl ether, and octadecyl vinyl ether. Branched vinyl ether compounds include, but are not limited to, isopropyl vinyl ether, isobutyl vinyl ether, sec-butyl vinyl ether, tert-butyl vinyl ether, and 2-ethyl hexyl vinyl ether. Cyclic vinyl ether compounds include, but are not limited to, cyclohexyl vinyl ether. Substituted vinyl ether compounds include, but are not limited to, hydroxybutyl vinyl ether.

Structures of exemplary vinyl-blocked bio-based polyfunctional carboxylic acids of the invention and their corresponding starting bio-based polyfunctional carboxylic acids and vinyl ether compounds are shown below in Table 3.

TABLE 3

Structures of exemplary vinyl-blocked bio-based polyfunctional carboxylic acids

| Bio-based polyfunctional carboxylic acids/vinyl ether compounds | Vinyl-blocked bio-based polyfunctional carboxylic acids |
|---|---|
| Azelaic acid (M.P. = 110° C.) | |
| Ethyl vinyl ether | |
| Citric acid (M.P. = 153° C.) | |
| Propyl vinyl ether | |

TABLE 3-continued

Structures of exemplary vinyl-blocked bio-based polyfunctional carboxylic acids

| Bio-based polyfunctional carboxylic acids/vinyl ether compounds | Vinyl-blocked bio-based polyfunctional carboxylic acids |
|---|---|
| 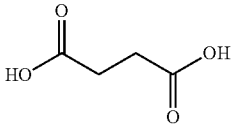<br>Succinic acid (M.P. = 185° C.) | 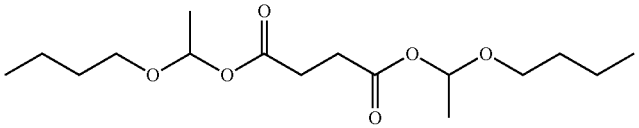 [SMILES: CCCCOC(C)OC(=O)CCC(=O)OC(C)OCCCC] |
| 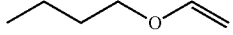<br>Butyl vinyl ether | |
| 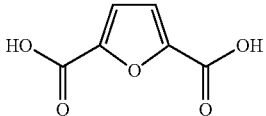<br>2,5-Furandicarboxylic acid (FDCA)<br>(M.P. > 300° C.) | 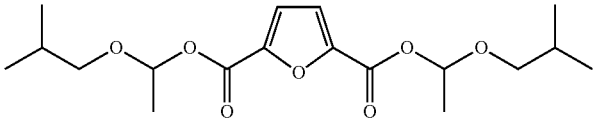 [SMILES: CC(C)COC(C)OC(=O)c1ccc(C(=O)OC(C)OCC(C)C)o1] |
| 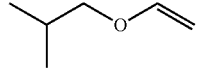<br>iso-Butyl vinyl ether | |

The vinyl-blocked bio-based polyfunctional carboxylic acids may be synthesized by a variety of methods. In one embodiment, the vinyl-blocked bio-based polyfunctional carboxylic acids are synthesized by reacting the at least one bio-based polyfunctional carboxylic acid with the at least one vinyl ether compound, at least one optional catalyst, and at least one optional solvent. In one embodiment, the molar ratio of vinyl groups in the at least one vinyl ether compound and carboxylic groups in the at least one bio-based polyfunctional carboxylic acid used for the synthesis of the vinyl-blocked bio-based polyfunctional carboxylic acids may range from 1.0:1.0 to 10:1, more preferably 4.0:1 to 6.0:1.0. Preferably, a stoichiometric excess of moles of vinyl ether groups relative to the carboxylic acid groups is used.

In one embodiment, the optional catalyst may be selected from phosphoric acid, hydrochloric acid, sulfuric acid, and the like. In a further embodiment, the optional catalyst may be present in an amount ranging from about 0.01% to about 5.0% by wt., preferably about 0.5% to about 2.0% by wt., even more preferably about 0.1% to about 1.0% by wt., of the total reaction mixture.

In one embodiment, the optional solvent may be selected from benzene, toluene, xylene, heptane, hexane, and the like. In a further embodiment, the optional solvent may be present in an amount ranging from about 0.1% to about 50.0% by wt., preferably about 0.5% to about 15.0% by wt., even more preferably about 1.0% to about 2.0% by wt., of the total reaction mixture. Solvents may be used during the synthesis to reduce viscosity and facilitate the synthesis reaction.

After reacting, the optional catalyst may be removed using a base, such as, for example, potassium hydroxide, in water via liquid-liquid extraction. Excess vinyl ether may be removed using known methods in the art, for example, rotary evaporation.

In one embodiment, the reaction to make the vinyl-blocked bio-based polyfunctional carboxylic acids of the invention may be carried out at temperatures dependent on the vinyl ether compound used. For example, a reaction temperature of about 30° C. may be used for ethyl vinyl ether, about 70° C. may be used for propyl vinyl ether, and about 80° C. may be used for butyl or isobutyl vinyl ether. In one embodiment, the reaction temperature may range from about 25° C. to about 100° C., more preferably, from about 30° C. to about 90° C., even more preferably, from about 50° C. to about 70° C.

Curable Coating Compositions Comprising Vinyl-Blocked Bio-Based Polyfunctional Acids and Polyfunctional Vegetable Oil-Based Epoxidized Resins The invention also relates to curable coating compositions comprising the vinyl-blocked bio-based polyfunctional carboxylic acids described above and polyfunctional vegetable oil-based epoxidized resins.

The polyfunctional vegetable oil-based epoxy resins include, but are not limited to, epoxidized vegetable oils, vegetable oil-based epoxy resins, and mixtures thereof. "Polyfunctional" as used herein in the phrase "polyfunctional vegetable oil-based epoxy resin" means the presence of two or more epoxide groups. Polyfunctional vegetable oil-based epoxy resins that may be used in the invention may be prepared in the manner disclosed in WO 2011/097484, the disclosure of which is incorporated by reference. For example, polyfunctional vegetable oil-based epoxy resins are prepared from the epoxidation of vegetable oil fatty acid esters of polyols having >4 hydroxyl groups/molecule. Polyol esters of fatty acids (PEFA's) containing four or more vegetable oil fatty acid moieties per molecule can be synthesized by the reaction of polyols with 4 or more hydroxyl groups per molecule with either a mixture of fatty acids or esters of fatty acids with a low molecular weight alcohol, as is known in the art. The former method is direct esterification while the latter method is transesterification. A catalyst may be used in the synthesis of these compounds. As shown in FIG. 1 with sucrose, as an exemplary polyol to be used in the invention, esterified with a vegetable oil fatty acid, epoxide groups may then be introduced by oxidation of the vinyl groups in the vegetable oil fatty acid to form epoxidized polyol esters of fatty acids (EPEFA's). The epoxidation may be carried out using reactions known in the art for the oxidation of vinyl groups with in situ epoxidation with peroxyacid being a preferred method.

Polyols having at least 4 hydroxyl groups per molecule suitable for the process include, but are not limited to, pentaerythritol, di-trimethylolpropane, di-pentaerythritol, tri-pentaerythritol, sucrose, glucose, mannose, fructose, galactose, raffinose, and the like. Polymeric polyols can also be used including, for example, copolymers of styrene and allyl alcohol, hyperbranched polyols such as polyglycidol and poly(dimethylpropionic acid), and the like. Exemplary polyols are shown below in Scheme 3 with the number of hydroxyl groups indicated by (f). Comparing sucrose to glycerol, there are a number of advantages for the use of a polyol having more than 4 hydroxyl groups/molecule including, but not limited to, a higher number of fatty acids/molecule; a higher number of unsaturations/molecule; when epoxidized, a higher number of oxiranes/molecule; and when crosslinked in a coating, higher crosslink density.

The degree of esterification may be varied. The polyol may be fully esterified, where substantially all of the hydroxyl groups have been esterified with the fatty acid, or it may be partially esterified, where only a fraction of the available hydroxyl groups have been esterified. It is understood in the art that some residual hydroxyl groups may remain even when full esterification is desired. In some applications, residual hydroxyl groups may provide benefits to the resin. Similarly, the degree of epoxidation may be varied from substantially all to a fraction of the available double bonds. The variation in the degree of esterification and/or epoxidation permits one of ordinary skill to select the amount of reactivity in the resin, both for the epoxidized resins and their derivatives.

Scheme 3

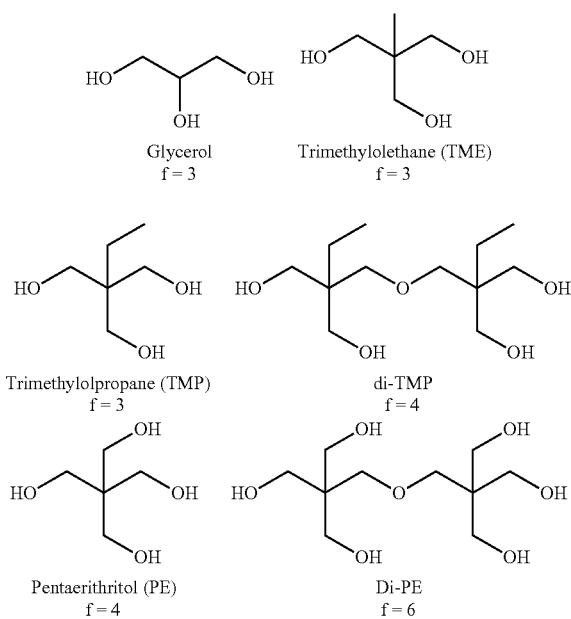

Glycerol
f = 3

Trimethylolethane (TME)
f = 3

Trimethylolpropane (TMP)
f = 3 di-TMP
f = 4

Pentaerithritol (PE)
f = 4

Di-PE
f = 6

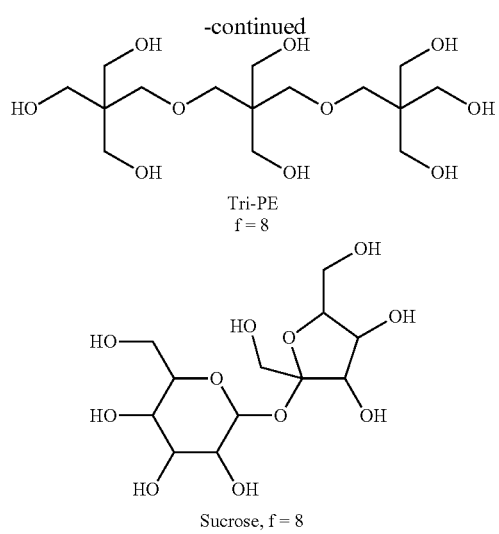

Tri-PE
f = 8

Sucrose, f = 8

The hydroxyl groups on the polyols can be either completely reacted or only partially reacted with fatty acid moieties. Any ethylenically unsaturated fatty acid may be used to prepare a polyol ester of fatty acids to be used in the invention, with polyethylenically unsaturated fatty acids, those with more than one double bond in the fatty acid chain, being preferred. The Omega 3, Omega 6, and Omega 9 fatty acids, where the double bonds are interrupted by methylene groups, and the seed and vegetable oils containing them may be used to prepare polyol ester of fatty acids to be used in the invention. Mixtures of fatty acids and of vegetable or seed oils, plant oils, may be used in the invention. The plant oils, as indicated above, contain mixtures of fatty acids with ethylenically unsaturated and saturated fatty acids possibly present depending on the type of oil. Examples of oils which may be used in the invention include, but are not limited to, corn oil, castor oil, soybean oil, safflower oil, sunflower oil, linseed oil, tall oil fatty acid, tung oil, vernonia oil, and mixtures thereof. As discussed above, the polyol fatty acid ester may be prepared by direct esterification of the polyol or by transesterification as is known in the art. The double bonds on the fatty acid moieties may be converted into epoxy groups using known oxidation chemistry yielding polyfunctional epoxy resins (EPEFA's)—epoxidized polyol esters of fatty acids. Table 4 lists the double bond functionality of some representative fatty acid esters (=/FA) based upon the number of esterified hydroxyl groups (f).

TABLE 4

Double Bond Functionality of Fatty Acids in Selected Oils

| Oil | Avg. =/FA | Functionality of = for FA esters having the indicated FA functionality | | | |
| --- | --- | --- | --- | --- | --- |
| | | f = 3 | f = 4 | f = 6 | f = 8 |
| Soybean | 1.54 | 4.62 | 6.16 | 9.24 | 12.32 |
| Safflower | 1.66 | 4.98 | 6.64 | 9.96 | 13.28 |
| Sunflower | 1.39 | 4.17 | 5.56 | 8.34 | 11.12 |
| Linseed | 2.10 | 6.30 | 8.40 | 12.60 | 16.80 |
| Tall Oil Fatty Acid | 1.37 | 4.11 | 5.48 | 8.22 | 10.96 |

The epoxidation of sucrose esters of ethylenically unsaturated vegetable oil fatty acids results in unique bio-based resins having a high concentration of epoxy groups. As has been seen, functionalities of 8 to 15 epoxide groups per molecule may be achieved, depending on the composition of the fatty acid used and the degree of substitution of the fatty acids on the sucrose moiety. This is substantially higher than what can be achieved through epoxidation of triglycerides which range from about 4 for epoxidized soybean oil up to 6 for epoxidized linseed oil.

The high epoxide functionality of these resins coupled with the rigidity of a polyol having at least 4 hydroxyl groups per molecule, such as sucrose, has significant implications for the use of these polyols and their derivatives in curable coating compositions of the invention. With the epoxidized polyol esters of fatty acids (EPEFA's), cross-linked materials having an outstanding combination of properties can be achieved.

Preferably, the polyfunctional vegetable oil-based epoxidized resin is selected from epoxidized sucrose soyate (ESS). As discussed above, fatty acids from soybean oil can be used to form esters with sucrose. Sucrose soyate (SS) has many positive properties that make it an ideal starting point for bio-based coatings, including that it is polyfunctional, has low viscosity (300-400 cP) with 100% solids, is 100% bio-based, and is commercially available. Sucrose, soybean oil, and sucrose soyate have the following structures:

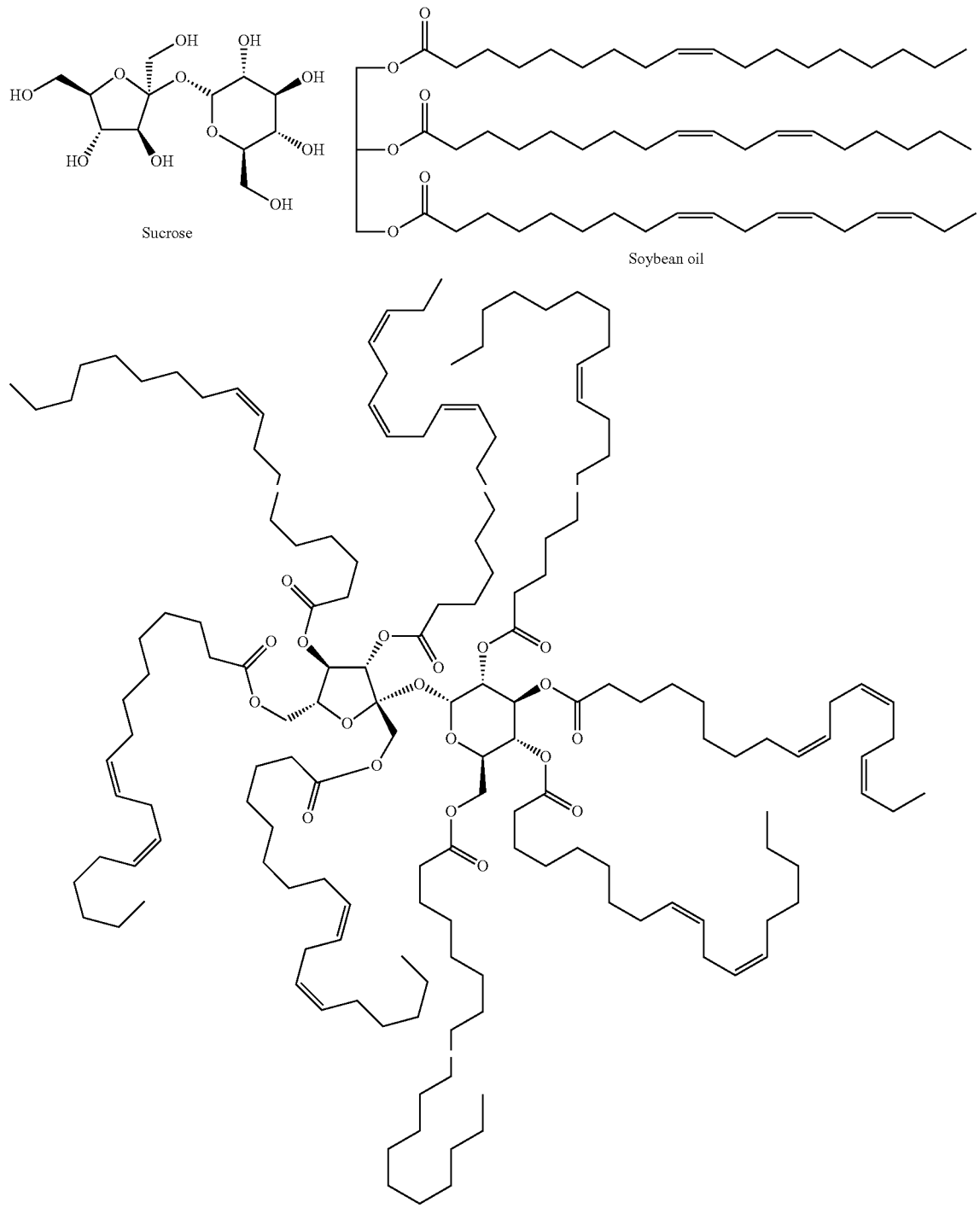

Sucrose Soyate

In contrast to SS, epoxidized sucrose soyate (ESS) is more versatile. Many types of coatings can be formed from ESS. Also, ESS has many beneficial properties, including 12 epoxy groups per molecule (epoxy equivalent weight of 270 g eq$^{-1}$), low viscosity (5,000 cP), 100% bio-based, easily synthesized, and is a clear and colorless resin. ESS can be synthesized in the manner disclosed in Pan et al., *Green Chemistry* 13:965-975 (2011), the disclosure of which is incorporated herein by reference. See also Scheme 4 below.

prepared by a variety of methods. In one embodiment, this method comprises combining the vinyl-blocked bio-based polyfunctional carboxylic acids described above with the polyfunctional vegetable oil-based epoxidized resins to make curable coating compositions of the invention. As a non-limiting example, the curable coating compositions can be prepared by combining the vinyl-blocked bio-based polyfunctional carboxylic acids, described above, and the polyfunctional vegetable oil-based epoxidized resins in the presence of at least one optional solvent, such as t-butyl acetate Scheme 4

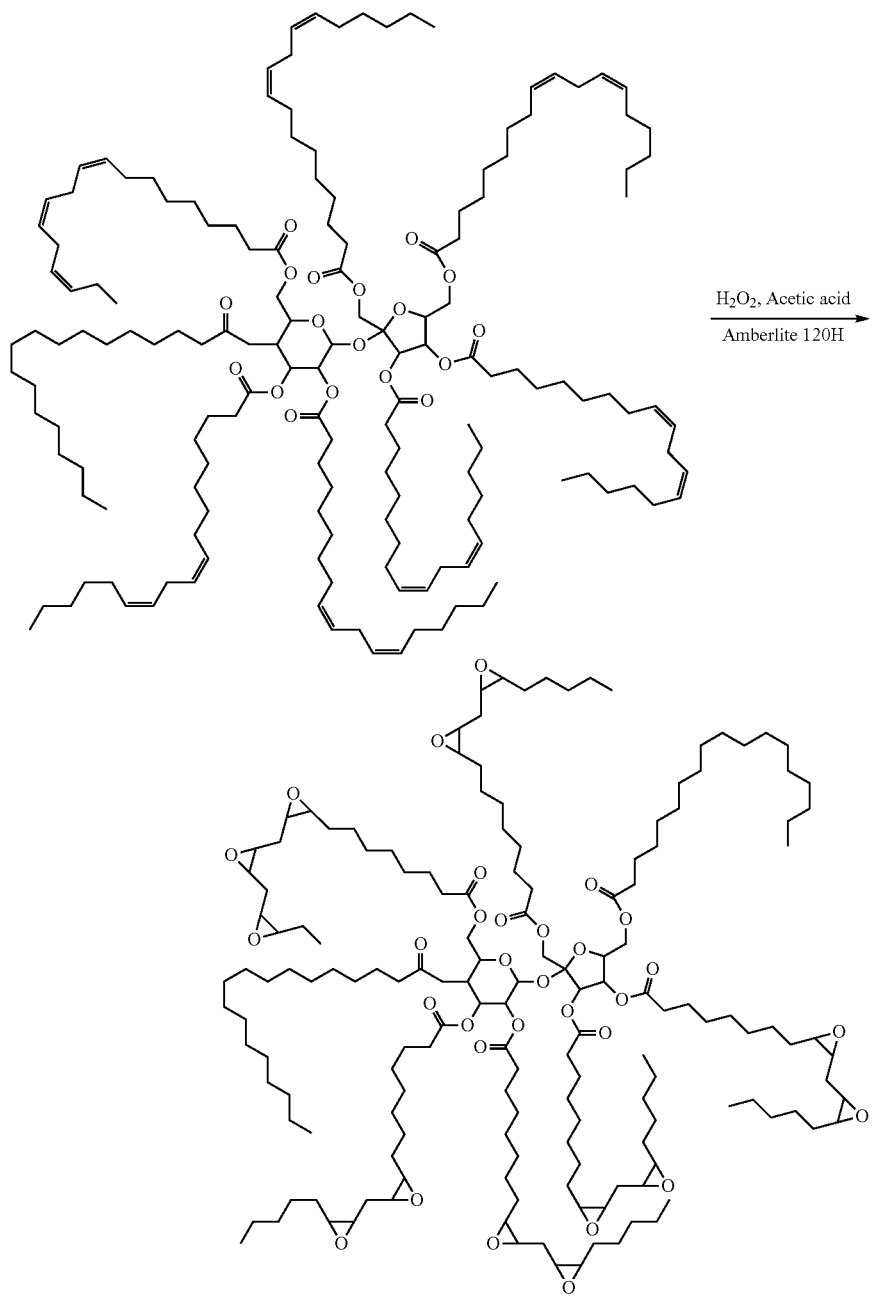

The curable coating compositions comprising the vinyl-blocked bio-based polyfunctional carboxylic acids and the polyfunctional vegetable oil-based epoxidized resins can be prepared by a variety of methods. (TBA), methyl n-amyl ketone (MAK), ethyl 3-ethoxypropionate (EEP), and at least one optional catalyst, such as dibutyltindilaurate (DBTDL).

In one embodiment, for the synthesis of the curable coating compositions of the invention, a stoichiometric equivalent amount of epoxide and blocked acid groups may be used. In another embodiment, the ratio of epoxy equivalents in the polyfunctional vegetable oil-based epoxidized resin to carboxylic equivalents in the vinyl-blocked bio-based polyfunctional carboxylic acids can be varied in order to vary the crosslink density and the properties of the curable coating composition.

The invention also relates to the use of a curable coating composition which may be coated onto a substrate and cured. The substrate can be any common substrate such as paper, polyester films such as polyethylene and polypropylene, metals such as aluminum and steel, glass, urethane elastomers, primed (painted) substrates, and the like. The invention also provides methods for coating such substrates by applying the curable coating composition to the substrate. The coating may be applied by methods know in the art such as drawdown, conventional air-atomized spray, airless spray, roller, brush. The curable coating composition of the invention may be cured thermally. Upon curing at elevated temperature, thermoset coating compositions of the invention have excellent hardness, solvent resistance, adhesion, and flexibility. In another embodiment of the invention, the invention relates to an article of manufacture comprising a thermoset coating composition of the invention.

A curable coating composition according to the invention may comprise a pigment (organic or inorganic) and/or other additives and fillers known in the art. For example a curable coating composition of the invention may further contain coating additives. Such coating additives include, but are not limited to, one or more leveling, rheology, and flow control agents such as silicones, fluorocarbons or cellulosics; extenders; reactive coalescing aids such as those described in U.S. Pat. No. 5,349,026, the disclosure of which is incorporated herein by reference; plasticizers; flatting agents; pigment wetting and dispersing agents and surfactants; ultraviolet (UV) absorbers; UV light stabilizers; tinting pigments; colorants; defoaming and antifoaming agents; anti-settling, anti-sag and bodying agents; anti-skinning agents; anti-flooding and anti-floating agents; biocides, fungicides and mildewcides; corrosion inhibitors; thickening agents; or coalescing agents. Specific examples of such additives can be found in Raw Materials Index, published by the National Paint & Coatings Association, 1500 Rhode Island Avenue, N.W., Washington, D.C. 20005. Further examples of such additives may be found in U.S. Pat. No. 5,371,148, incorporated herein by reference.

Examples of flatting agents include, but are not limited to, synthetic silica, available from the Davison Chemical Division of W. R. Grace & Company as SYLOID®; polypropylene, available from Hercules Inc., as HERCOFLAT®; synthetic silicate, available from J. M. Huber Corporation, as ZEOLEX®.

Examples of viscosity, suspension, and flow control agents include, but are not limited to, polyaminoamide phosphate, high molecular weight carboxylic acid salts of polyamine amides, and alkylene amine salts of an unsaturated fatty acid, all available from BYK Chemie U.S.A. as ANTI TERRA®. Further examples include, but are not limited to, polysiloxane copolymers, polyacrylate solution, cellulose esters, hydroxyethyl cellulose, hydroxypropyl cellulose, polyamide wax, polyolefin wax, hydroxypropyl methyl cellulose, polyethylene oxide, and the like.

Solvents may also be added to the curable coating compositions in order to reduce the viscosity. Hydrocarbon, ester, ketone, ether, ether-ester, alcohol, or ether-alcohol type solvents may be used individually or in mixtures. Examples of solvents can include, but are not limited to benzene, toluene, xylene, aromatic 100, aromatic 150, acetone, methylethyl ketone, methyl amyl ketone, butyl acetate, t-butyl acetate, tetrahydrofuran, diethyl ether, ethylethoxy propionate, isopropanol, butanol, butoxyethanol, and so on.

EXAMPLES

Example 1

Synthesis of Blocked-Azelaic Acid Compounds
(Table 5)

In a 50-mL single neck round bottom flask, azelaic acid (5.00 g, 0.0266 mol) was combined with 4 molar equivalents (0.106 mol) of the appropriate vinyl ether compound (7.66 g of ethyl vinyl ether, 9.15 g of propyl vinyl ether, or 10.64 g of butyl or isobutyl vinyl ether). To this mixture, solid phosphoric acid (0.017 g, 0.177 mmol) was added. The mixture was stirred for 5 hours at a temperature dependent on the vinyl ether compound used (30° C. for ethyl vinyl ether, 70° C. for propyl vinyl ether, or 80° C. for butyl or isobutyl vinyl ether). After the reaction mixture cooled to room temperature, it was transferred to a 125-mL separatory funnel, where 40 mL of 0.05 M KOH was added. The funnel was capped and shaken to extract the phosphoric acid. The organic layer was isolated, and rotary evaporation was used to remove the excess vinyl ether. Blocked-azelaic acid compounds were recovered in 84-94% yield. Example $^1$H NMR data for propyl vinyl ether blocked azelaic acid (CDCl$_3$, δ, ppm): 0.81 (triplet, 6H, CH$_3$), 1.234 (singlet, 6H, O2C—CH2-CH2-CH$_2$—CH$_2$—CH$_2$—CH2-CH2-CO2), 1.274 and 1.287 (singlet, 6H, O—CH(CH$_3$)—O), 1.49 (multiplet, 8H, O2C—CH2-CH$_2$ and O—CH2-CH$_2$—CH3), 2.21 (triplet, 4H, O2C—CH$_2$), 3.49 (quartet, 4H, O—CH$_2$—CH2-CH3), 5.82 and 5.83 (quartet, 2H, O—CH(CH3)—O). A small amount of single blocked molecules is present, as evident by some peak splitting and a small carboxylic acid peak present in the NMR.

Example 2

Synthesis of Blocked-Succinic Acid Compounds
(Table 5)

The procedure used for blocking azelaic acid compounds was used for their succinic acid equivalents, using 5.00 g succinic acid and the properly adjusted amounts of vinyl ether and phosphoric acid. Example $^1$H NMR data for propyl vinyl ether blocked succinic acid (CDCl$_3$, δ, ppm): 0.83 (triplet, 6H, —CH$_3$), 1.30 (multiplet, 4H, O—CH(CH$_2$)—O), 1.50 (quartet, 4H, O—CH2-CH$_2$—CH3), 2.56 (triplet, 4H, O2C—CH$_2$—CH$_2$—CO2), 3.33 (quartet, 4H, O—CH$_2$—CH2-CH3), 5.86 and 5.87 (s, 2H, O—CH(CH2)-O). The presence of other peaks suggests that the product is 3:1 mixture of two blocked carboxylic acids per molecule to one blocked carboxylic acid per molecule.

Example 3

Synthesis of Blocked-Citric Acid Compounds
(Table 5)

In a 50-mL single neck round bottom flask, citric acid (5.00 g, 0.0260 mol) was combined with 6 molar equivalents (0.156 mol) of the appropriate vinyl ether compound (13.45 g of propyl vinyl ether or 15.64 g of butyl or isobutyl vinyl ether). To this mixture, solid phosphoric acid (0.026 g, 0.260 mmol) was added. The mixture was stirred for 18 hours using the same temperatures used for the block-azelaic acid synthesis. The phosphoric acid was extracted using 40 mL of 0.05 M KOH, and the excess vinyl ether was removed via rotary evaporation. Blocked-citric acid compounds were recovered in 84-94% yield.

Example 4

Synthesis of isobutyl vinyl ether blocked 2,5-furandicarboxylic acid (Table 5)

In a 50-mL single neck round bottom flask, 2,5-furandicarboxylic acid (FDCA; 5.00 g, 0.0320 mol) was combined with isobutyl vinyl ether (IBVE; 12.83 g, 0.128 mol) and solid phosphoric acid (0.021 g, 0.214 mmol). The mixture was stirred for 18 hours at 80° C. The phosphoric acid was extracted using 40 mL of 0.05 M KOH. The organic layer was filtered using a Buchner funnel, and the excess isobutyl vinyl ether was removed from the filtered liquid via rotary evaporation. This resulted in 6.40 g of IBVE-FDCA (56% yield) being recovered, along with the recovery of 1.76 g of unreacted FDCA (80% of the unreacted starting material).

TABLE 5

Structure of vinyl ether blocked acids produced

| Blocked Acid Name Abbreviation | Structure |
|---|---|
| Ethyl vinyl ether blocked succinic acid EVE-SuA | 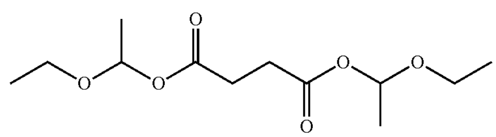 [SMILES: CCOC(C)OC(=O)CCC(=O)OC(C)OCC] |
| Propyl vinyl ether blocked succinic acid PVE-SuA | 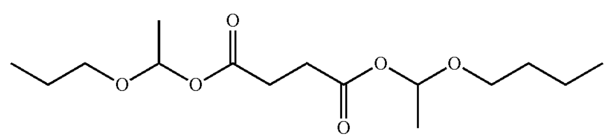 [SMILES: CCCCOC(C)OC(=O)CCC(=O)OC(C)OCCC] |
| Butyl vinyl ether blocked succinic acid BVE-SuA | 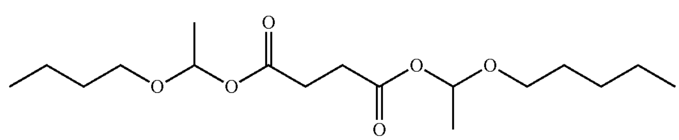 [SMILES: CCCCCOC(C)OC(=O)CCC(=O)OC(C)OCCCC] |
| Isobutyl vinyl ether blocked succinic acid IBVE-SuA | 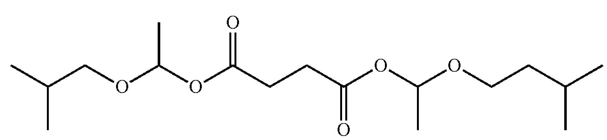 [SMILES: CC(C)CCOC(C)OC(=O)CCC(=O)OC(C)OCC(C)C] |
| Ethyl vinyl ether blocked azelaic acid EVE-AzA | 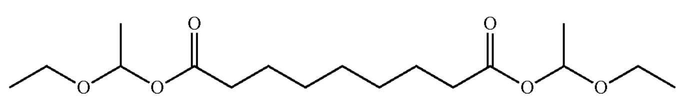 [SMILES: CCOC(C)OC(=O)CCCCCCCC(=O)OC(C)OCC] |
| Propyl vinyl ether blocked azelaic acid PVE-AzA | 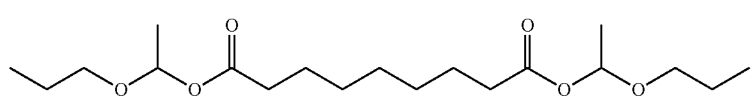 [SMILES: CCCOC(C)OC(=O)CCCCCCCC(=O)OC(C)OCCC] |
| Butyl vinyl ether blocked azelaic acid BVE-AzA | 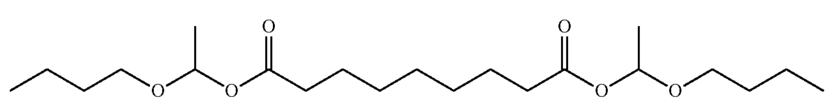 [SMILES: CCCCOC(C)OC(=O)CCCCCCCC(=O)OC(C)OCCCC] |
| Isobutyl vinyl ether blocked azelaic acid IBVE-AzA | 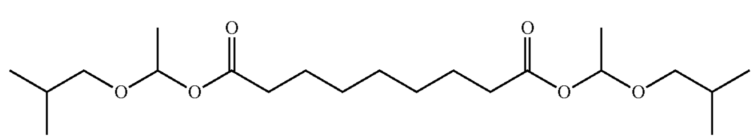 [SMILES: CC(C)COC(C)OC(=O)CCCCCCCC(=O)OC(C)OCC(C)C] |
| Ethyl vinyl ether blocked citric acid EVE-CiA | 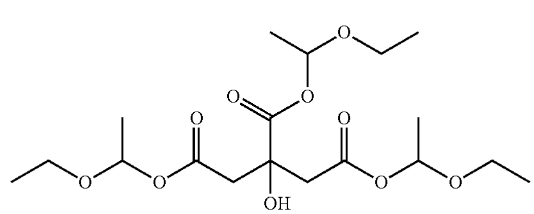 [SMILES: CCOC(C)OC(=O)CC(O)(CC(=O)OC(C)OCC)C(=O)OC(C)OCC] |

TABLE 5-continued

Structure of vinyl ether blocked acids produced

| Blocked Acid Name Abbreviation | Structure |
|---|---|
| Propyl vinyl ether blocked citric acid PVE-CiA | [structure] |
| Butyl vinyl ether blocked citric acid BVE-CiA | [structure] |
| Isobutyl vinyl ether blocked citric acid IBVE-CiA | [structure] |
| Isobutyl vinyl ether blocked 2,5-furandicarboxylic acid IBVE-FDCA | [structure] |

Example 5

Coating Formulation Method

Coating formulations were made using a 1:1 mole ratio of epoxide to acid and 5% 1,8-Diazabicyclo[5.4.0]undec-7-ene (DBU) by total weight. For example, epoxidized sucrose soyate (ESS, 5.00 g, 0.0188 equivalents), ethyl vinyl ether blocked azelaic acid (EVE-AzA, 3.12 g, 0.0188 equivalents), and DBU (0.41 g, 0.0027 equivalents) were combined in a formulation cup. The mixture was hand stirred to obtain a consistent solution.

Coating Application and Curing.

A Gardco wet film applicator was used to apply a 4 mil thick layer of each formulation onto Bonderite 1000 treated steel and glass substrates. The substrates were then placed in an oven preheated to 170° C., where they were allowed to cure for 4 hours.

Measurement of Coating Properties.

Figure 2:
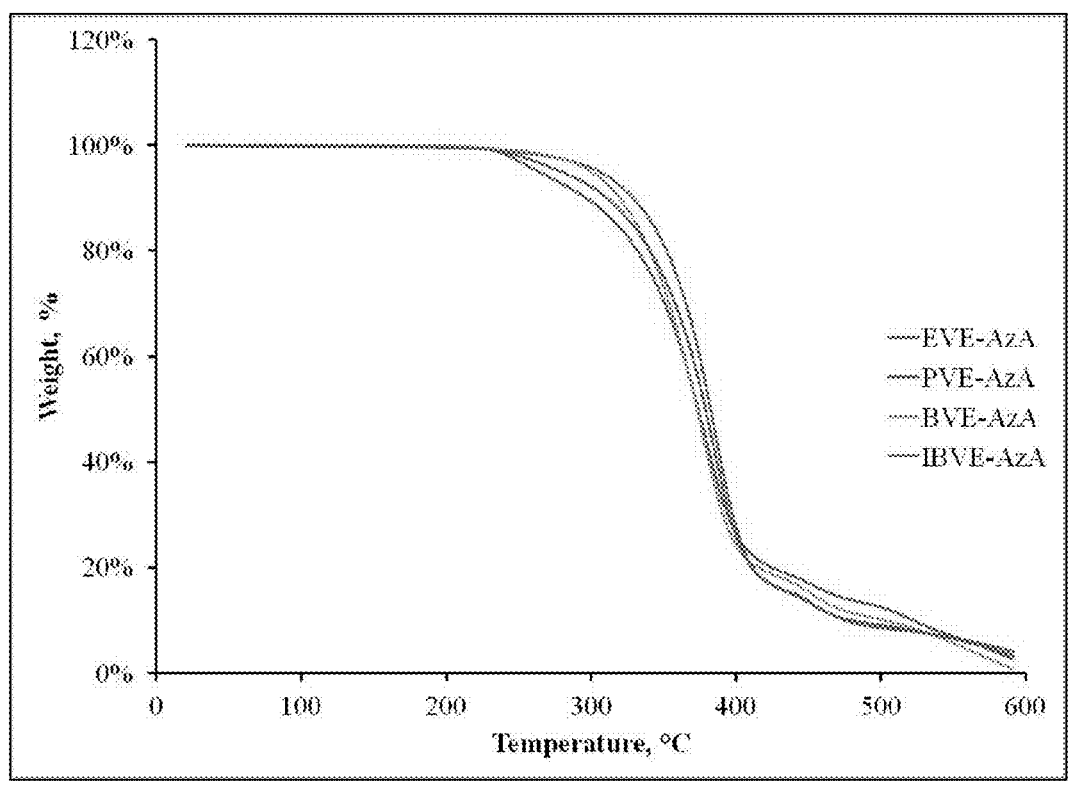
FIG. 2 depicts the thermogravimetric analysis of cured coatings made using epoxidized sucrose soyate and azeleic acid (AzA) blocked by different vinyl ether compounds.
Figure 3:
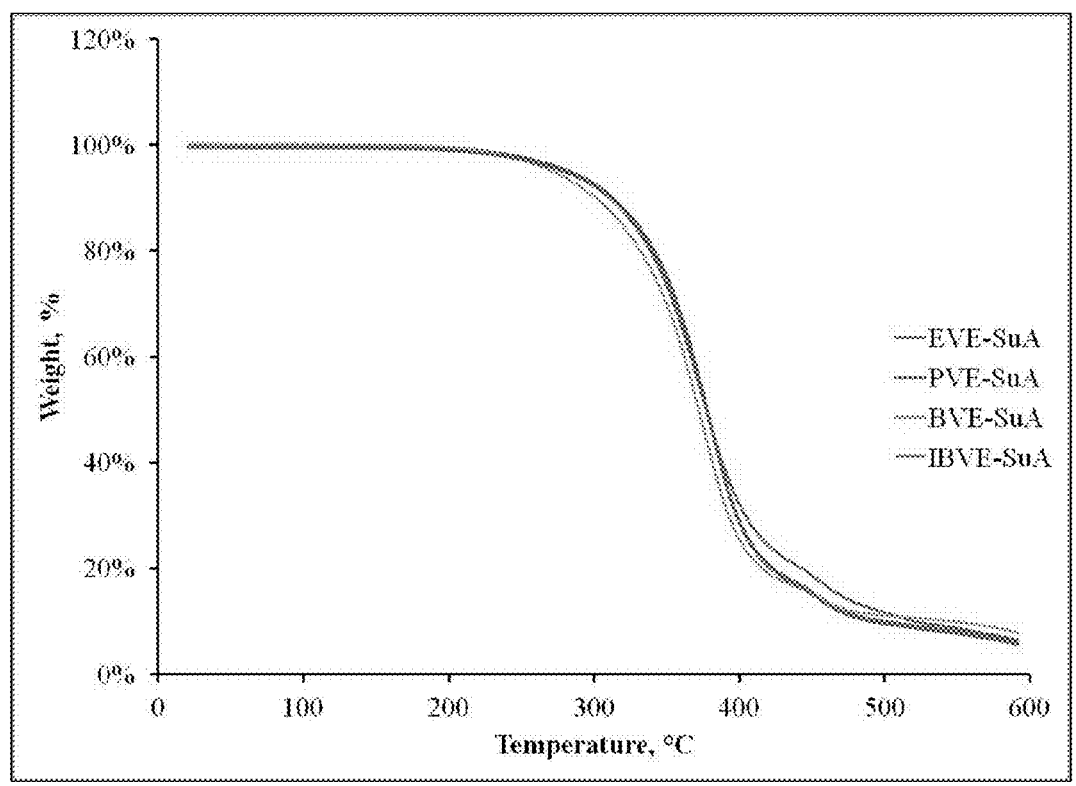
FIG. 3 depicts the thermogravimetric analysis of cured coatings made using epoxidized sucrose soyate and succinic acid (SuA) blocked by different vinyl ether compounds.
Figure 4:
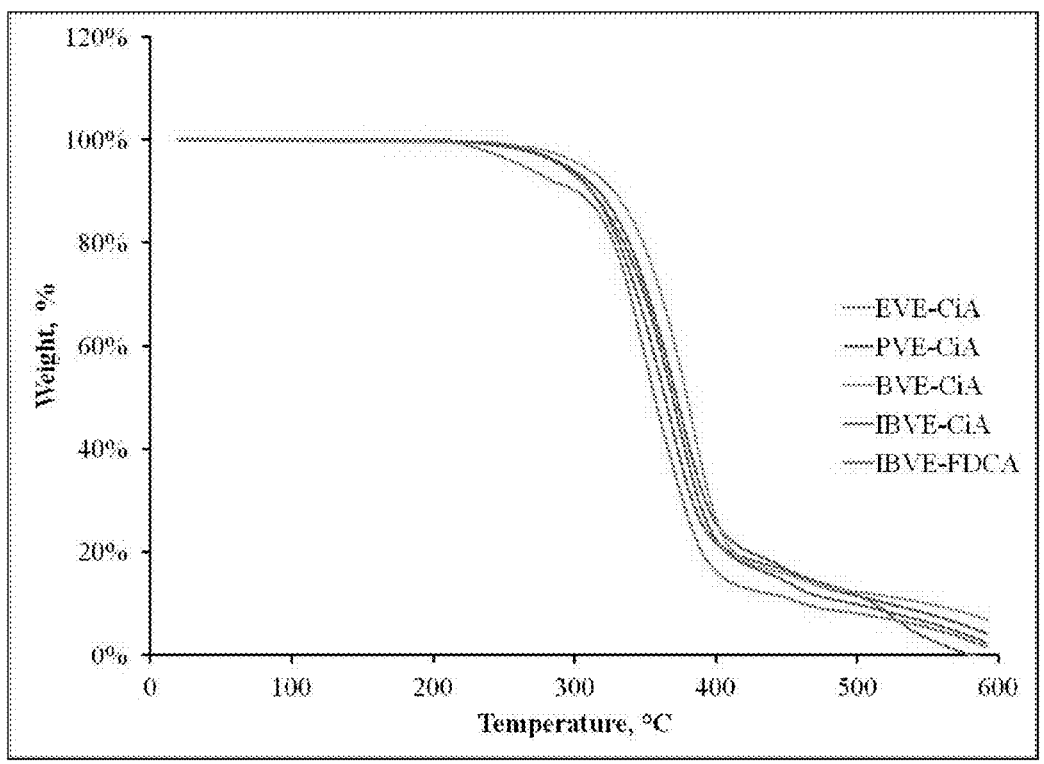
FIG. 4 depicts the thermogravimetric analysis of cured coatings made using epoxidized sucrose soyate and citric acid (CiA) blocked by different vinyl ether compounds and furan dicarboxylic acid (FDCA) blocked by isobutyl vinyl ether (IBVE).

Dried film thickness was measured on the steel panels using a Byko-test 8500 (Table 6). Konig hardness of the films was measured using a Byk Gardner pendulum hardness tester on the steel panels (Table 6). Pencil hardness, crosshatch adhesion, MEK double rubs, and reverse impact were measured for dried films on steel panels (Table 6). Thermogravimetric analysis was performed by removing a sample of each coating from the glass substrate and was analyzed using a TA Instruments Q-Series 500 Thermogravimetric analyzer (Table 7). $T_{10\%}$ is the temperature at 10 percent weight loss. FIGS. 2-4 depict the thermogravimetric analysis of the cured coatings.

TABLE 6

Dry film properties of ESS and blocked acid thermosets prepared

| Blocked Acid | Film Thickness | Konig Hardness | Pencil Hardness | Crosshatch Adhesion | MEK Double Rubs | Reverse Impact |
|---|---|---|---|---|---|---|
| EVE-Azelaic Acid | 20.1 ± 8.0 μm | 96.3 ± 7.6 | 3H | 5B | 400+ | >168 in · lb |
| PVE-Azelaic Acid | 23.1 ± 5.2 μm | 49.7 ± 1.5 | 3H | 5B | 400+ | >168 in · lb |
| BVE-Azelaic Acid | 13.2 ± 5.4 μm | 82.0 ± 4.4 | 3H | 5B | 400+ | >168 in · lb |
| IBVE-Azelaic Acid | 11.2 ± 3.4 μm | 93.7 ± 4.2 | 2H | 5B | 400+ | >168 in · lb |
| EVE-Succinic Acid | 24.6 ± 11.8 μm | 24.7 ± 7.5 | 3B | 5B | 400+ | 160 in · lb |

TABLE 6-continued

Dry film properties of ESS and blocked acid thermosets prepared

| Blocked Acid | Film Thickness | Konig Hardness | Pencil Hardness | Crosshatch Adhesion | MEK Double Rubs | Reverse Impact |
|---|---|---|---|---|---|---|
| PVE-Succinic Acid | 28.4 ± 3.6 μm | 20.3 ± 0.6 | 2B | 5B | 400+ | >168 in · lb |
| BVE-Succinic Acid | 33.7 ± 8.7 μm | 18.7 ± 2.9 | 2B | 5B | 400+ | >168 in · lb |
| IBVE-Succinic Acid | 25.8 ± 5.1 μm | 25.0 ± 1.0 | 2B | 5B | 400+ | >168 in · lb |
| EVE-Citric Acid | 104 ± 25 μm | 56.3 ± 1.5 | 3H | 0B | 70 | 8 in · lb |
| PVE-Citric Acid | 74.1 ± 50.9 μm | 18.7 ± 0.6 | 3B | 2B | 50 | 20 in · lb |
| BVE-Citric Acid | 49.3 ± 28.4 μm | 24.0 ± 1.0 | <EE | 3B | 100 | 40 in · lb |
| IBVE-Citric Acid | 38.8 ± 20.5 μm | 67.7 ± 3.2 | HB | 0B | 100 | 40 in · lb |
| IBVE-FDCA | 52.9 ± 5.3 μm | 55.7 ± 3.2 | H | 5B | 380 | 140 in · lb |

TABLE 7

Thermal stability of cured coating formulations, as determined by TGA

| Blocked Acid | $T_{10\%}$, °C |
|---|---|
| EVE-Azelaic Acid | 329 |
| PVE-Azelaic Acid | 297 |
| BVE-Azelaic Acid | 319 |
| IBVE-Azelaic Acid | 311 |
| EVE-Succinic Acid | 313 |
| PVE-Succinic Acid | 311 |
| BVE-Succinic Acid | 301 |
| IBVE-Succinic Acid | 311 |
| EVE-Citric Acid | 312 |
| PVE-Citric Acid | 317 |
| BVE-Citric Acid | 328 |
| IBVE-Citric Acid | 312 |
| IBVE-FDCA | 304 |

Example 6

Figure 5:
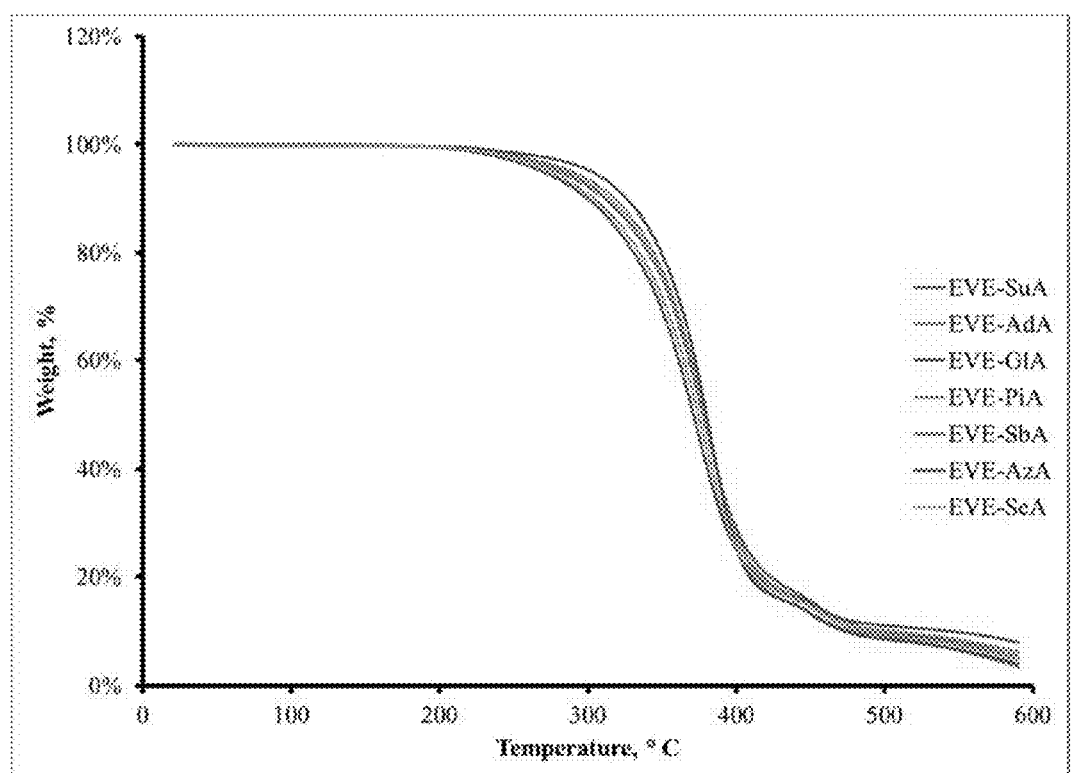
FIG. 5 depicts the thermogravimetric analysis of cured coatings made using epoxidized sucrose soyate and ethyl vinyl ether (EVE) blocked acids (succinic (SuA), adipic (AdA), glutaric (GlA), pimelic (PiA), subaric (SbA), azeleic (AzA), and sebacic (SeA)).

Synthesis of Additional Ethyl Vinyl Ether-Blocked Bio-Based Polyfunctional Carboxylic Acids, Curable Coatings Containing the Same and Epoxide Sucrose Soyate, and Properties Thereof The procedures used to synthesize the vinyl-blocked bio-based polyfunctional carboxylic acid compounds above were used to make the following ethyl vinyl ether (EVE)-blocked bio-based polyfunctional carboxylic acids: EVE-succinic acid (EVE-SuA), EVE-glutaric acid (EVE-GlA), EVE-adipic acid (EVE-AdA), EVE-pimelic acid (EVE-PiA), EVE-suberic acid (EVE-SbA), EVE-azelaic acid (EVE-AzA), and EVE-sebacic acid (EVE-SeA). See Table 8. Coating compositions containing these vinyl-blocked bio-based polyfunctional carboxylic acid compounds and epoxide sucrose soyate (ESS) were made, applied, cured, and properties measured (Table 9) in the same manner as the coating compositions above. FIG. 5 depicts the thermogravimetric analysis of these cured coatings.

TABLE 8

Structure of ethyl vinyl ether blocked acids produced

| Blocked Acid Name Abbreviation | Structure |
|---|---|
| Ethyl vinyl ether blocked succinic acid EVE-SuA | [structure] |
| Ethyl vinyl ether blocked glutaric acid EVE-GlA | [structure] |
| Ethyl vinyl ether blocked adipic acid EVE-AdA | [structure] |
| Ethyl vinyl ether blocked pimelic acid EVE-PiA | [structure] |
| Ethyl vinyl ether blocked suberic acid EVE-SbA | [structure] |

TABLE 8-continued

Structure of ethyl vinyl ether blocked acids produced

| Blocked Acid Name Abbreviation | Structure |
|---|---|
| Ethyl vinyl ether blocked azelaic acid EVE-AzA | 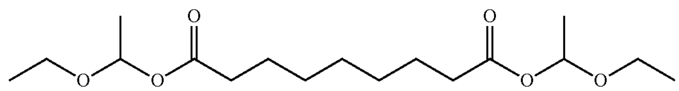 [SMILES: CCOC(C)OC(=O)CCCCCCCC(=O)OC(C)OCC] |
| Ethyl vinyl ether blocked sebacic acid EVE-SeA | 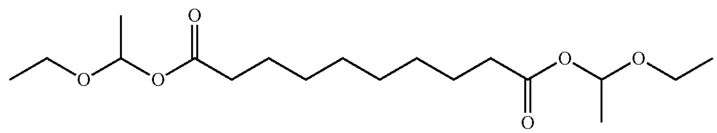 [SMILES: CCOC(C)OC(=O)CCCCCCCCC(=O)OC(C)OCC] |

TABLE 9

Dry film properties of ESS and ethyl vinyl ether blocked acid thermosets prepared

| Blocked Acid | Film Thickness | Konig Hardness | Pencil Hardness | Crosshatch Adhesion | MEK Double Rubs | Reverse Impact |
|---|---|---|---|---|---|---|
| EVE-Succinic Acid | 24.6 ± 11.8 μm | 25 | 3B | 5B | 400+ | >168 in · lb |
| EVE-Glutaric Acid | 20.2 ± 10.9 μm | 27 | 2B | 5B | 400+ | >168 in · lb |
| EVE-Adipic Acid | 21.9 ± 5.5 μm | 157 | B | 5B | 400+ | >168 in · lb |
| EVE-Pimelic Acid | 16.6 ± 1.7 μm | 160 | HB | 5B | 400+ | >168 in · lb |
| EVE-Suberic Acid | 29.5 ± 3.1 μm | 135 | H | 5B | 400+ | >168 in · lb |
| EVE-Azelaic Acid | 15.3 ± 7.1 μm | 170 | 3H | 5B | 400+ | >168 in · lb |
| EVE-Sebacic Acid | 25.8 ± 5.7 μm | 115 | HB | 5B | 400+ | >168 in · lb |

CONCLUSIONS

Azelaic acid, succinic acid, and FDCA have superior solvent resistance, adhesion, and flexibility. Higher hardness of azelaic acid compared to the others suggests a higher crosslinked system is produced. The poor properties of citric acid based coatings suggest a lower inter-ESS crosslinked network is formed.

The claimed invention is:

1. A curable coating composition comprising:
   a) at least one vinyl-blocked bio-based polyfunctional carboxylic acid compound comprising the reaction product of:
      i) at least one bio-based polyfunctional carboxylic acid; and
      ii) at least one vinyl ether compound;
   b) at least one polyfunctional vegetable oil-based epoxy resin;
   c) at least one catalyst;
   d) optionally, at least one solvent, at least one other additive, or mixture thereof; and
   e) optionally, at least one pigment.

2. The curable coating composition of claim 1, wherein for the vinyl-blocked bio-based polyfunctional carboxylic acid said at least one bio-based polyfunctional carboxylic acid is selected from dicarboxylic acids, tricarboxylic acids, or mixtures thereof.

3. The curable coating composition of claim 1, wherein for the vinyl-blocked bio-based polyfunctional carboxylic acid said at least one bio-based polyfunctional carboxylic acid is saturated or ethylenically unsaturated.

4. The curable coating composition of claim 1, wherein for the vinyl-blocked bio-based polyfunctional carboxylic acid said at least one bio-based polyfunctional carboxylic acid is optionally substituted.

5. The curable coating composition of claim 1, wherein for the vinyl-blocked bio-based polyfunctional carboxylic acid said at least one bio-based polyfunctional carboxylic acid is aromatic or non-aromatic.

6. The curable coating composition of claim 1, wherein for the vinyl-blocked bio-based polyfunctional carboxylic acid said at least one bio-based polyfunctional carboxylic acid is selected from oxalic acid, succinic acid, glutaric acid, adipic acid, pimelic acid, suberic acid, azelaic acid, sebacic acid, brassylic acid, citric acid, furan dicarboxylic acid, and tartaric acid.

7. The curable coating composition of claim 1, wherein for the vinyl-blocked bio-based polyfunctional carboxylic acid said at least one vinyl ether compound is linear, branched, or cyclic.

8. The curable coating composition of claim 1, wherein for the vinyl-blocked bio-based polyfunctional carboxylic acid said at least one vinyl ether compound is selected from ethyl vinyl ether, propyl vinyl ether, butyl vinyl ether, and isobutyl vinyl ether.

9. The curable coating composition of claim 1, wherein for the vinyl-blocked bio-based polyfunctional carboxylic acid the molar ratio of vinyl groups in said at least one vinyl ether compound and carboxylic groups in said at least one bio-based polyfunctional carboxylic acid range from 1.0:1.0 to 10:1.

10. The curable coating composition of claim 1, wherein said vinyl-blocked bio-based polyfunctional carboxylic acid is selected from one of the following:

31
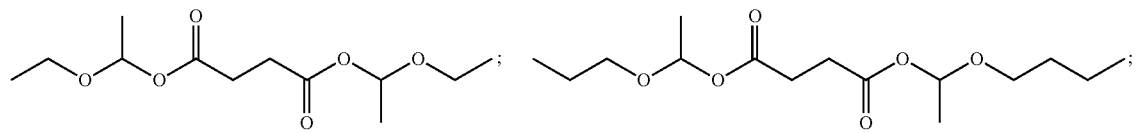
32
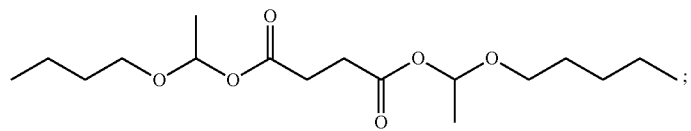
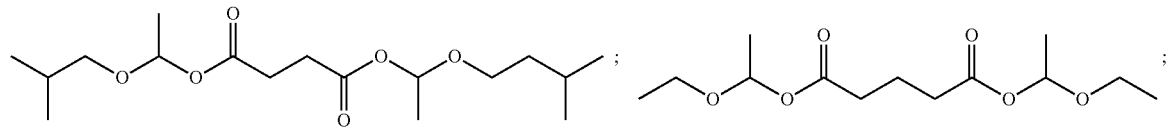
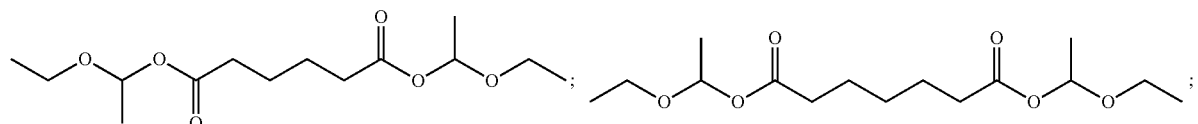
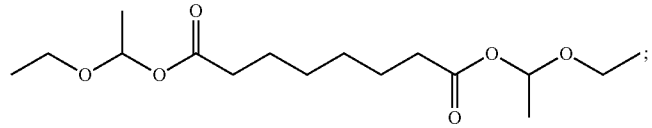
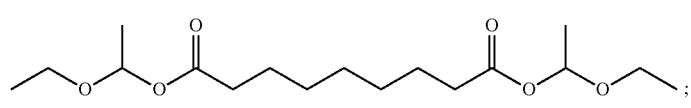
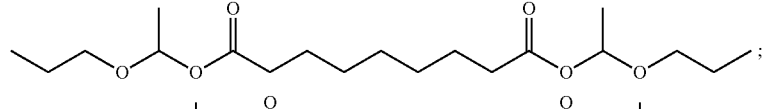
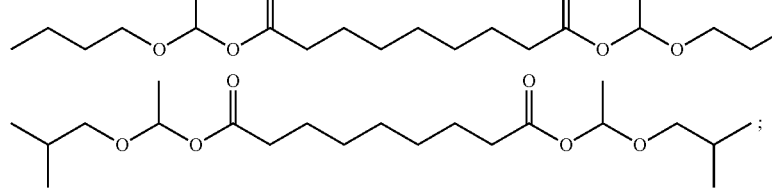
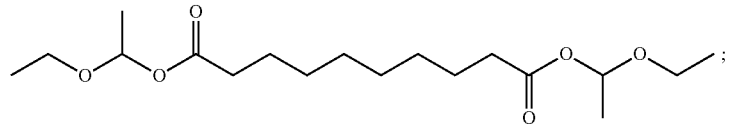
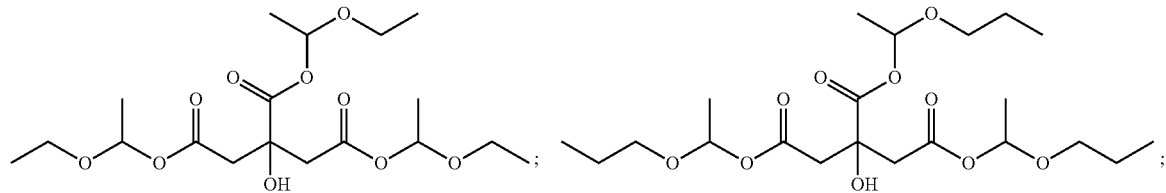
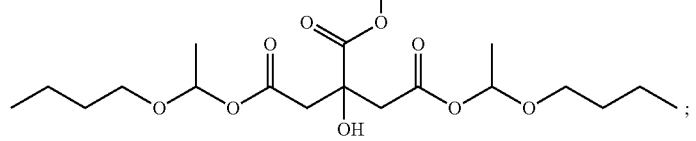

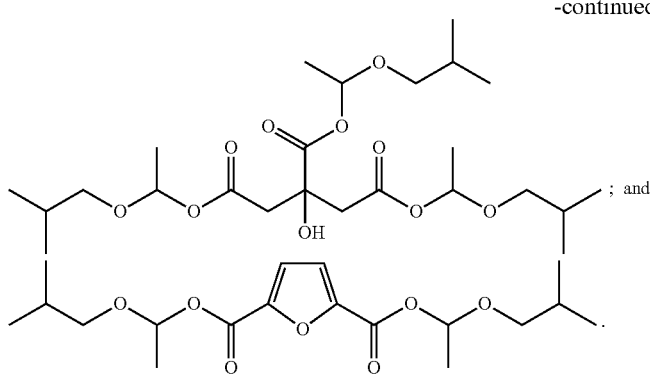

; and

11. The curable coating composition of claim 1, wherein said at least one polyfunctional vegetable oil-based epoxy resin is prepared by the epoxidation of at least one vegetable oil fatty acid ester of a polyol having more than four hydroxyl groups per molecule.

12. The curable coating composition of claim 11, wherein said at least one vegetable oil fatty acid ester of a polyol is prepared by the reaction of at least one polyol with four or more hydroxyl groups per molecule with a mixture of fatty acids or esters of fatty acids with a low molecular weight alcohol.

13. The curable coating composition of claim 12, wherein said polyol with four or more hydroxyl groups per molecule is selected from pentaerythritol, di-trimethylolpropane, di-pentaerythritol, tri-pentaerythritol, sucrose, glucose, mannose, fructose, galactose, and raffinose.

14. The curable coating composition of claim 13, wherein said fatty acids are selected from ethylenically unsaturated fatty acids, saturated fatty acids, or mixtures thereof.

15. The curable coating composition of claim 14, wherein said at least one vegetable oil fatty acid ester of a polyol having more than four hydroxyl groups per molecule is sucrose soyate.

16. The curable coating composition of claim 1, wherein said at least one polyfunctional vegetable oil-based epoxy resin is an epoxidized vegetable oil, vegetable oil-based epoxy resin, or mixture thereof.

17. An object coated with the curable coating composition of claim 1.

18. A method of making a vinyl-blocked bio-based polyfunctional carboxylic acid, comprising the step of reacting at least one bio-based polyfunctional carboxylic acid with at least one vinyl ether compound, at least one optional catalyst, and at least one optional solvent.

19. A method of making a curable coating composition of claim 1, comprising the step of mixing at least one vinyl-blocked bio-based polyfunctional carboxylic acid compound with at least one polyfunctional vegetable oil-based epoxy resin.

* * * * *